United States Patent
Yang (10) Patent No.: US 8,905,758 B2
(45) Date of Patent: Dec. 9, 2014

(54) SYSTEM AND METHOD FOR MANUFACTURING A DENTAL IMPLANT SURGICAL GUIDE

(75) Inventor: Been-Der Yang, Taipei (TW)

(73) Assignee: Saturn Imaging Inc., Taipei (TW)

( * ) Notice: Subject to any disclaimer, the term of this patent is extended or adjusted under 35 U.S.C. 154(b) by 0 days.

(21) Appl. No.: 12/722,774

(22) Filed: Mar. 12, 2010

(65) Prior Publication Data

US 2010/0233647 A1 Sep. 16, 2010

(30) Foreign Application Priority Data

Mar. 13, 2009 (TW) ................................ 98108315 A (51) Int. Cl.
*A61C 3/02* (2006.01)
*A61C 1/08* (2006.01)

(52) U.S. Cl.
CPC ...................................... *A61C 1/084* (2013.01)
USPC ......................................................... 433/75

(58) Field of Classification Search
USPC ............ 433/29, 72, 75, 202.1, 231, 215, 213, 433/55, 66; 700/97, 98, 118, 197, 198
See application file for complete search history.

(56) References Cited

U.S. PATENT DOCUMENTS

| | | | |
|---|---|---|---|
| 5,562,448 A * | 10/1996 | Mushabac | 433/215 |
| 5,604,677 A * | 2/1997 | Brien | 700/186 |
| 5,768,134 A | 6/1998 | Swaelens et al. | |
| 5,967,777 A * | 10/1999 | Klein et al. | 433/75 |
| 6,030,211 A * | 2/2000 | Sandhaus | 433/76 |
| 6,073,058 A * | 6/2000 | Cossen et al. | 700/184 |
| 6,296,483 B1 | 10/2001 | Champleboux | |
| 6,814,575 B2 | 11/2004 | Poirier | |
| 7,331,786 B2 * | 2/2008 | Poirier | 433/75 |
| 2001/0044094 A1* | 11/2001 | Schostek et al. | 433/51 |
| 2005/0163342 A1* | 7/2005 | Persky | 382/103 |
| 2006/0257817 A1* | 11/2006 | Shelton | 433/75 |
| 2008/0193896 A1 | 8/2008 | Yang et al. | |

* cited by examiner

*Primary Examiner* — Cris L Rodriguez
*Assistant Examiner* — Matthew Seward
(74) *Attorney, Agent, or Firm* — Muncy, Geissler, Olds & Lowe, P.C.

(57) ABSTRACT

A system and a method for manufacturing a dental implant surgical guide are disclosed. The dentist may obtain a cast model of the patient's jaw and a plurality of CT images of the jawbone and teeth by CT scanning. The system includes a cast model navigation device, a controlling module, and a computer system. The navigation device includes an articulated arm capable of holding a tool and a plurality of braking elements. The articulated arm is operated to measure the positions of markers on the cast model to provide the position registration between the cast model and the plurality of CT images. Once registered, the articulated arm is operated to simulate the target implant position under the guidance of the CT images. The arm can then be locked via the plurality of braking elements controlled by the controlling module for manufacturing of the surgical guide.

4 Claims, 10 Drawing Sheets

SYSTEM AND METHOD FOR MANUFACTURING A DENTAL IMPLANT SURGICAL GUIDE

BACKGROUND OF THE INVENTION

1. Field of the Invention

The present invention relates to a system and a method for manufacturing a surgical guide, and more particularly, to a system and a method which can precisely and quickly manufacture a surgical guide with a dental cast model.

2. Description of the Related Art

In order to help patients with missing teeth to restore their chewing function, dental implant placement is an effective and mature treatment. Generally, dental implant treatment uses a titanium-based alloy stud placed in the jawbone to imitate the root of a natural tooth. After some time, when the osseointegration between the jawbone and the dental implant is completed, subsequent prosthetic treatment proceeds. Compared with the traditional tooth bridge treatment, which requires that the healthy neighboring teeth be trimmed to support the bridge, dental implant treatment does not affect the neighboring teeth and is obviously a superior and more efficient treatment.

The position and the direction of the dental implant have great impacts on the quality of the treatment. An improper position of the implant will cause excessive stress when the patient is chewing, and the implant could eventually come out due to bone loss. The appropriate implant position depends on two factors: thorough planning of the surgery and precise drilling during the surgery. In surgery planning, the dentist must use the patient's cast model and X-ray radiographs to plan for the optimal implant position. The cast model provides external information for the dentist to evaluate the patient's occlusion status to achieve better results in the treatment. On the other hand, X-ray radiographs can provide internal anatomical information on the teeth, jawbone, alveolar nerve, paranasal sinus, etc. While drilling during the surgery, the dentist has to rely on his/her clinical experience and surgical skill to operate successfully. Therefore, the dentist's ability to perform stable drilling and strong perception of the 3D space can affect the quality of the surgery. An experienced dentist often uses the neighboring teeth and the exposed bone ridge as references, guided by the surgery plan, to place the implant in the optimal position.

As technology advances, computed tomography (CT) and surgical guides are now applied in dental implant surgery to improve the quality thereof. Compared to traditional planar imaging methods such as periapical film or panoramic imaging, CT provides a 1:1 undistorted image of the patient's oral anatomy. Therefore, the dentist can use the CT image with 3D imaging software to develop a surgery plan more accurately and then, can manufacture a corresponding surgical guide to guide the drill in order to place the implant in the optimal position. The surgical guide is usually made out of dental resin materials by forming a crown across the neighboring teeth. A metal ring is disposed at the implant position, and guiding sleeves of different apertures are used during the surgery to accommodate drill bits of different sizes. The CT-based surgical guide not only provides stability during drilling but also ensures placement in the optimal implant position prescribed in the surgery plan by the 3D imaging software.

A traditional manufacturing process for a CT-based surgical guide is illustrated below:

Step 1: Manufacturing a CT scan appliance. The CT scan appliance is manufactured out of dental resins and functions like a removable crown, which comprises a plurality of radiopaque markers. The image of the marker will appear in the CT image of the patient to provide the spatial association between the CT image and the surgical guide manufacturing system. Hence, the implant position planned in 3D imaging software can be transferred to the surgical guide system in order to manufacture the guide accurately. In addition to the markers, the CT scan appliance can also include wax-up information made of barium sulfate material to provide the ideal prosthetic information as the guideline for the implant placement.

Step 2: The patient wears the CT scan appliance for CT scan.

Step 3: Using 3D imaging software for surgery planning. The dentist uses imaging software to load the CT images of the patient to show the anatomical image of the jawbone around the surgery area. The anatomical information and the ideal prosthetic information of the CT scan appliance help the dentist to determine the optimal implant position, which will meet the occlusion demand but also will provide a stable foundation for implant placement as well. In addition to the dental prosthetic and jawbone information, scanning data of the gum surface can also be loaded to provide a more comprehensive 3D virtual reality of the patient's oral cavity.

Step 4: Transferring the planning to manufacture the surgical guide. First of all, a position registration must be obtained between the image space (CT image) and physical space (manufacturing system). The registration is obtained by the help of the markers of the CT scan appliance. By identifying the positions of the markers in the CT image and measuring the positions of the markers in physical space, the spatial transformation between the image and physical spaces can be calculated to facilitate the registration. Once registered, the planned implant position in the imaging software can be precisely transferred to the surgical guide manufacturing system for fabrication. Currently, there are two types of techniques for manufacturing CT surgical guides: rapid prototyping and CNC drilling. The rapid prototyping technique is disclosed in U.S. Pat. No. 5,768,134, while the CNC drilling technique is disclosed in U.S. Pat. Nos. 5,967,777, 6,296, 483B1, and 6,814,575 B2.

Although the CT surgical guide technique can provide a way for improving the quality of the implant treatment, it is not widely used in clinical cases. One of the reasons is that dentists are not familiar with 3D imaging software for surgery planning. In fact, dentists spend most of the time using tools in the real environment of the patient's oral cavity and the corresponding cast model. They are not trained to use the computer mouse to manipulate virtual images in the complicated 3D imaging software. At present, most dentists use plaster cast models and X-ray radiographs, including CT images, for surgery planning. Although dentists have to mentally map relationships between the cast model and the images themselves, the cast model provides a closer situation to the real condition of the patient's oral cavity as compared with the 3D virtual reality provided by software. Therefore, this invention proposes a dental implant surgery planning system based on the cast model in U.S. Patent Publication No. 2008-0193896. The system navigates on the cast model by providing a real time 3D jawbone image corresponding to the interested location on the cast model. The association eliminates the burden of the mental conversion between the anatomical image and the location on the cast model for dentists. Another disadvantage of the current surgical guide manufacturing technique is that surgery planning and guide manufacturing are performed separately, When dentists finish a surgery plan, they have to send the surgery plan to a third party service for manufacture of the surgical guide. It is time consuming and, besides, it is not possible to verify the accuracy of the surgical guide, making it less acceptable in actual application. Therefore, it is desirable to integrate the dental implant surgery planning and the surgical guide manufacturing into one system to improve the accuracy of the guide and to reduce the time required for manufacturing.

Therefore, it is necessary to develop an integrated surgical guide manufacturing system to provide the familiar dental implant planning environment for dentists or dental technicians and also to generate a precise surgical guide promptly.

SUMMARY OF THE INVENTION

It is an object of the present invention to provide a system for manufacturing a surgical guide based on the cast model to allow the dentist precisely and quickly to manufacture a surgical guide with the cast model.

In order to achieve the above object, the present invention consists of a surgical guide manufacturing system for a dental implant surgery plan, which comprises obtaining a cast model of a patient's jaw, making a CT scan appliance with a plurality of radiopaque markers out of the cast model, and having the patient wear the CT scan appliance to obtain a plurality of CT images of the patient's jaw and teeth. The system comprises a cast model navigation device, a controlling module, and a computer system. The cast model navigation device is provided for navigating the cast model. The cast model navigation device comprises an articulated arm, a plurality of decoders, and a plurality of braking elements. The articulated arm is provided for holding a tool, and the articulated arm can move with multiple degrees of freedom. The plurality of decoders is provided for measuring the movement information of the articulated arm, and the plurality of braking elements is provided for locking the articulated arm. The controlling module is electrically connected with the cast model navigation device for obtaining the movement information and controlling the activation or deactivation of the plurality of the braking elements. The computer system is electrically connected with the controlling module, with the computer system comprising a memory and a processor. The memory is provided for storing a software program and the plurality of CT images. The processor is electrically connected with the memory for executing the software program. The articulated arm is operated to measure the positions of the markers of the CT scan appliance mounted on the cast model to provide position registration between the cast model and the plurality of CT images. The articulated arm is operated to move to an implant position. The articulated arm can be locked via the plurality of braking elements controlled by the controlling module, for manufacturing a surgical guide.

A surgical guide manufacturing method using the surgical guide manufacturing system for a dental implant surgery planning includes: providing a cast model navigation device, with the cast model navigation device comprising an articulated arm for holding a tool; obtaining position registration between the cast model and the plurality of CT images; operating the articulated arm to move to an implant position on the cast model; locking the articulated arm; and applying and curing a curable material around the implant position to form a surgical guide.

DETAILED DESCRIPTION OF THE PREFERRED EMBODIMENTS

The advantages and innovative features of the invention will become more apparent from the following detailed description when taken in conjunction with the accompanying drawings.

Figure 1:
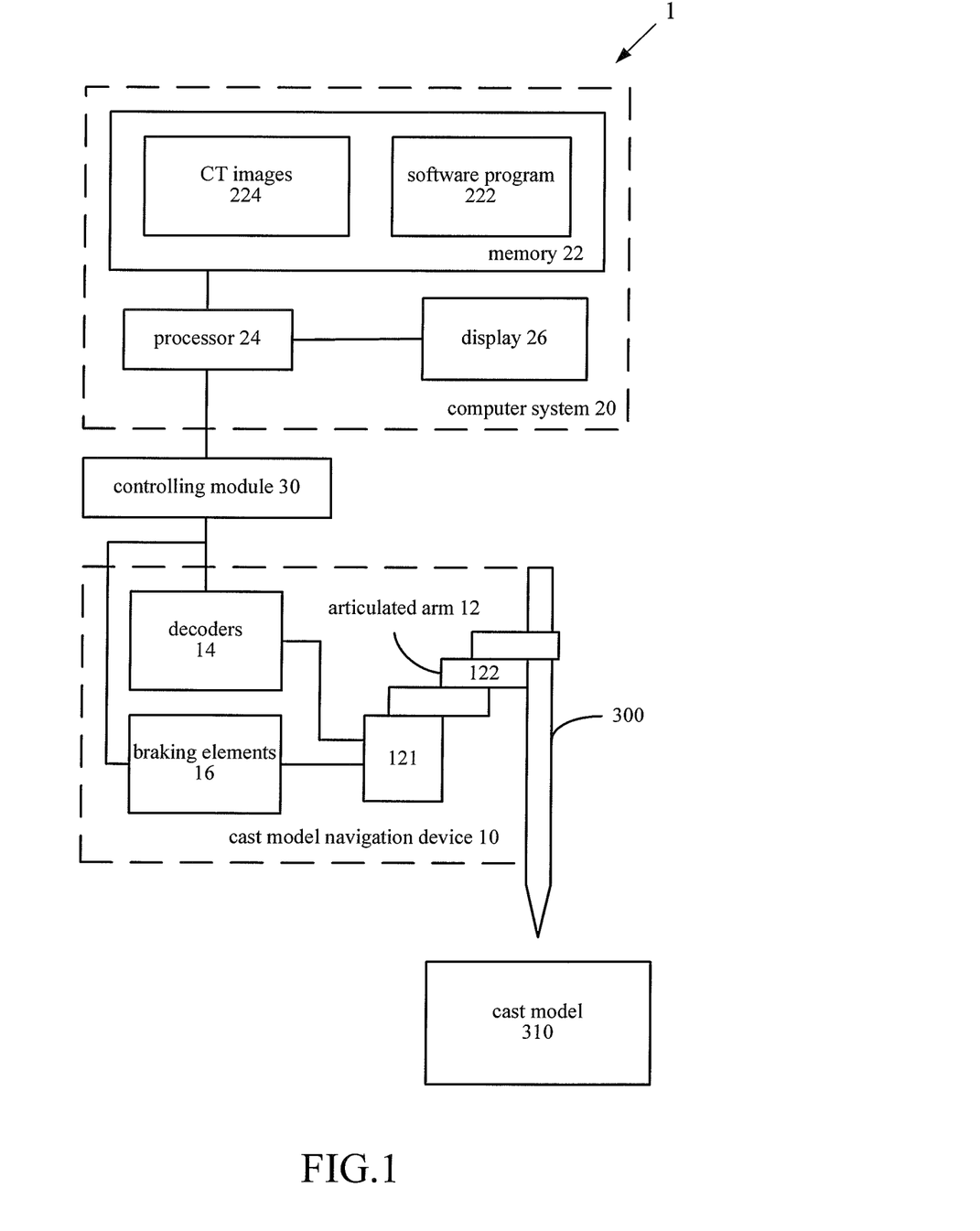
FIG. 1 illustrates a view of a surgical guide manufacturing system in the present invention.

Please refer to FIG. 1 for a view of a surgical guide manufacturing system 1 in the present invention. The surgical guide manufacturing system 1 is provided for planning a dental implant surgery to help dentists accurately fabricate surgical guides. Before planning the surgery, the dentist produces a cast model of a patient's jaw and makes a CT scan appliance with a plurality of radiopaque markers out of the cast model. Then, the patient wears the CT scan appliance to obtain a plurality of CT images of the patient's jaw and teeth. The plurality of CT images can show the images of the plurality of markers for position registration. However, the above steps are known in the art and will not be further described for the sake of brevity.

As shown in FIG. 1, the surgical guide manufacturing system 1 comprises a cast model navigation device 10, a controlling module 30, and a computer system 20. The cast model navigation device 10 navigates on the cast model 310. The controlling module 30 is electrically connected with the cast model navigation device 10 and the computer system 20. The controlling module 30 can be an independent device or a device selectively integrated in the cast model navigation device 10 or the computer system 20. The cast model navigation device 10 comprises an articulated arm 12, a plurality of decoders 14, and a plurality of braking elements 16. The articulated arm 12 comprises a base 121 and a moving element set 122. One end of the moving element set 122 is movably connected to the base 121, and the other end can hold a tool 300. The moving element set 122 comprises a plurality of moving elements so as to let the moving element set 122 drive the tool 300 to move with multiple degrees of freedom with respect to the base 121 and to move the articulated arm 12 to the implant position. The moving element set 122 can be a set of serially connected moving linkages, a parallel moving mechanism, or other combination structure which can move with multiple degrees of freedom. The tool 300 can be a probe, a drill, or other surgical device. The plurality of decoders 14 and the plurality of braking elements 16 are each disposed respectively at connecting points between the moving element set 122 and the base 121, and connecting points between the moving elements. The plurality of decoders 14 and the plurality of braking elements 16 are electrically connected with the controlling module 30. According to different designs of the moving element set 122, the plurality of decoders 14 is implemented with linear or rotary decoders, as is the plurality of braking elements 16. The plurality of decoders 14 measures the movement information of the articulated arm 12 and transmits it to the controlling module 30. The movement information can be the coordinates or the amount of movement of the articulated arm 12. The plurality of braking elements 16 can be activated to lock the articulated arm 12 via the controlling module 30.

The computer system 20 comprises a memory 22 and a processor 24. The memory 22 stores a software program 222 and a plurality of CT images 224. The processor 24 is electrically connected with the memory 22 to execute the software program 222. The articulated arm 12 is operated to control the tool 300 to measure the corresponding position of the CT scan appliance on the cast model 310, thereby obtaining the movement information at the corresponding position of the articulated arm 12 via the plurality of decoders 14. This movement information can be transmitted to the computer system 20 via the controlling module 30. Thereafter, the software program 222 combines the movement information and the plurality of CT images 224 to obtain the position registration between the cast model 310 and the plurality of CT images 224 to enable the user to obtain the information related to the implant position when the user moves the articulated arm 12 to the implant position.

The controlling module 30 is electrically connected with the processor 24 of the computer system 20 and with the plurality of decoders 14 and the plurality of braking elements 16 of the cast model navigation device 10. Then the controlling module 30 may obtain the movement information of the articulated arm 12 and control the activation and deactivation of the plurality of braking elements 16. The controlling module 30 may comprise a processing unit and a memory for processing and obtaining the movement information and other related information. When the user moves the articulated arm 12 to the ideal implant position, he/she can operate the controlling module 30 to store the movement information of the articulated arm 12 corresponding to the implant position. Since the user may have to move the articulated arm 12 away from implant position to change the tool 300 or for other purposes, when the articulated arm 12 is first moved to the implant position, the movement information of the articulated arm 12 corresponding to the implant position is obtained from the plurality of decoders 14 via the controlling module 30 for storage. When the articulated arm 12 is once again moved back to the implant position, the controlling module 30 will compare the previously stored movement information with the movement information corresponding to the actual position of the articulated arm 12 to see if the two sets of information match. If so, then, the controlling module 30 activates the plurality of braking elements 16 to fix the articulated arm 12 at the implant position. The controlling module 30 may further comprise a keypad device for the user to control the controlling module 30 for storing the information. Furthermore, the user can use a software interface of the computer system 20 to operate the controlling module 30 to execute the above functions.

In addition, the computer system 20 can receive implant position information corresponding to the implant position planned or loaded by a user via the software program 222, and the software program 222 will convert the implant position information into the movement information corresponding to the implant position. Therefore, when the articulated arm 12 is moved to the implant position in accordance with the movement information, the controlling module 30 can activate the plurality of braking elements 16 to lock the articulated arm 12. For example, the user can plan in advance an ideal implant position via the software program of the computer system 20, and store implant position information in the computer system 20. The user can also obtain implant position information corresponding to an implant position from another source and load it into the computer system 20. When the user wants to use the surgical guide manufacturing system 1 of the present invention to manufacture the surgical guide corresponding to the implant position, the computer system 20 can use the software program 222 to process and transfer the information to obtain the movement information corresponding to the implant position for the articulated arm 12, and then to transmit the movement information to the controlling module 30. The controlling module 30 uses the movement information as a reference value. When the articulated arm 12 is moved to the position designated by the movement information, the controlling module 30 can activate the plurality of braking elements 16 immediately to lock the articulated arm 12.

Figure 2:
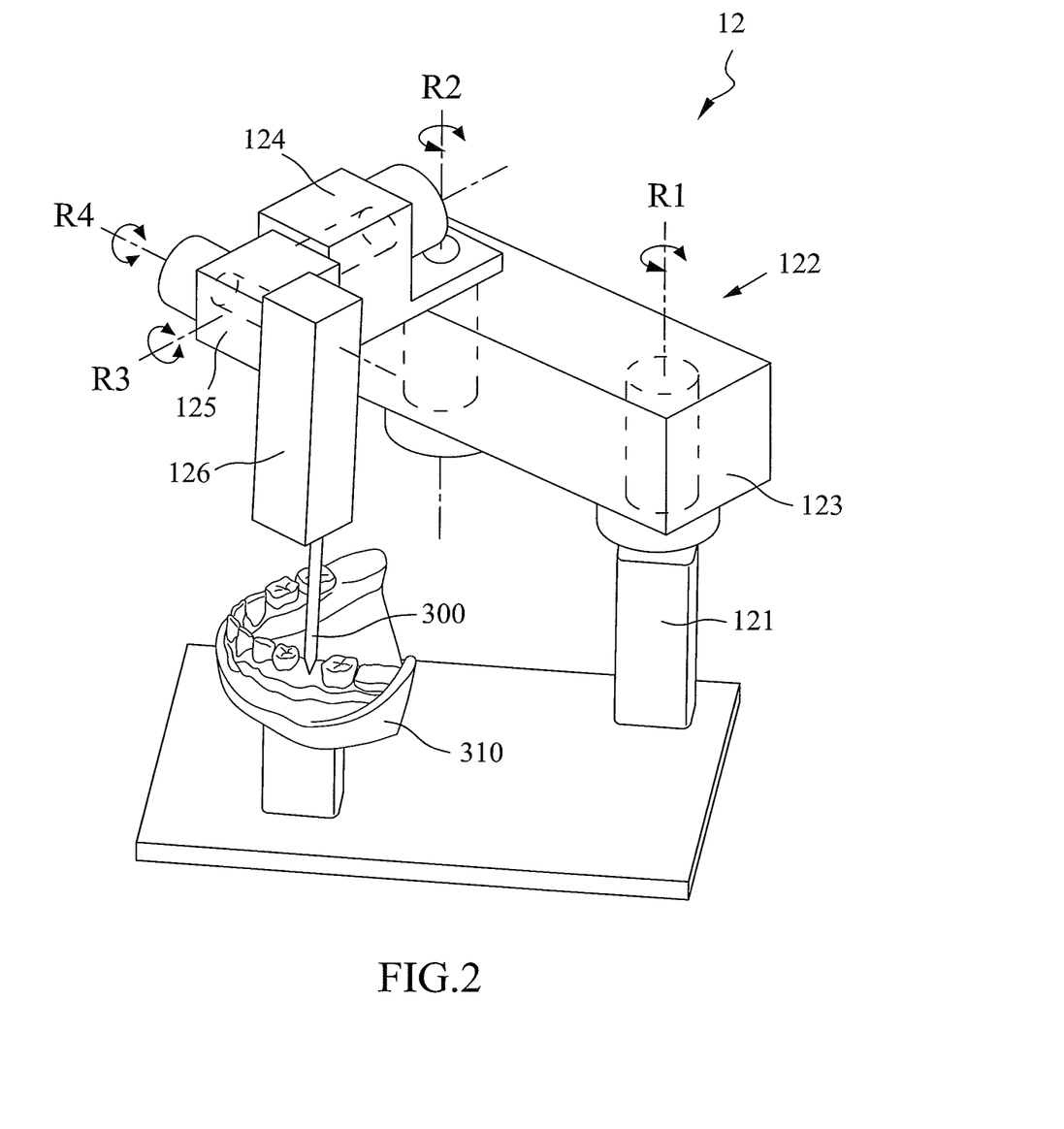
FIG. 2 illustrates an embodiment view of a cast model navigation device of the surgical guide manufacturing system in the present invention.

Please refer to FIG. 2 for an embodiment view of a cast model navigation device of the surgical guide manufacturing system 1 in the present invention. As shown in FIG. 2, in this embodiment, the articulated arm 12 of the cast model navigation device 10 comprises a base 121 and a moving element set 122. The moving element set 122 comprises a first moving element 123, a second moving element 124, a third moving element 125, and a positioning module 126. The first moving element 123 has both ends axially connected with the base 121 and the second moving element 124, respectively. The second moving element 124 has both ends axially connected with the first moving element 123 and the third moving element 125, respectively. The third moving element 125 has both ends axially connected with the second moving element 124 and the positioning module 126, respectively.

The first moving element 123 can rotate with respect to a first rotating axis R1, the second moving element 124 can rotate with respect to a second rotating axis R2, and the first rotating axis R1 is substantially parallel to the second rotating axis R2. Therefore, the first moving element 123 and the second moving element 124 can move together to drive the third moving element 125 to move arbitrarily on a plane. The third moving element 125 can rotate with respect to a third rotating axis R3, and the third rotating axis R3 is substantially orthogonal to the second rotating axis R2. Therefore, the third moving element 125 can drive the positioning module 126 to rotate with respect to the third rotating axis R3. The positioning module 126 itself can rotate with respect to a fourth rotating axis R4, and the fourth rotating axis R4 is substantially orthogonal to the third rotating axis R3 to enable the positioning module 126 to rotate in different directions.

By using the above structure, the articulated arm 12 is operated to achieve at least four degrees of freedom (including arbitrary movement on a plane and rotating along two axes), so the dentist can freely operate the tool 300 on the cast model 310 to determine the implant position (that is, the axis direction of the tool).

Figure 3:
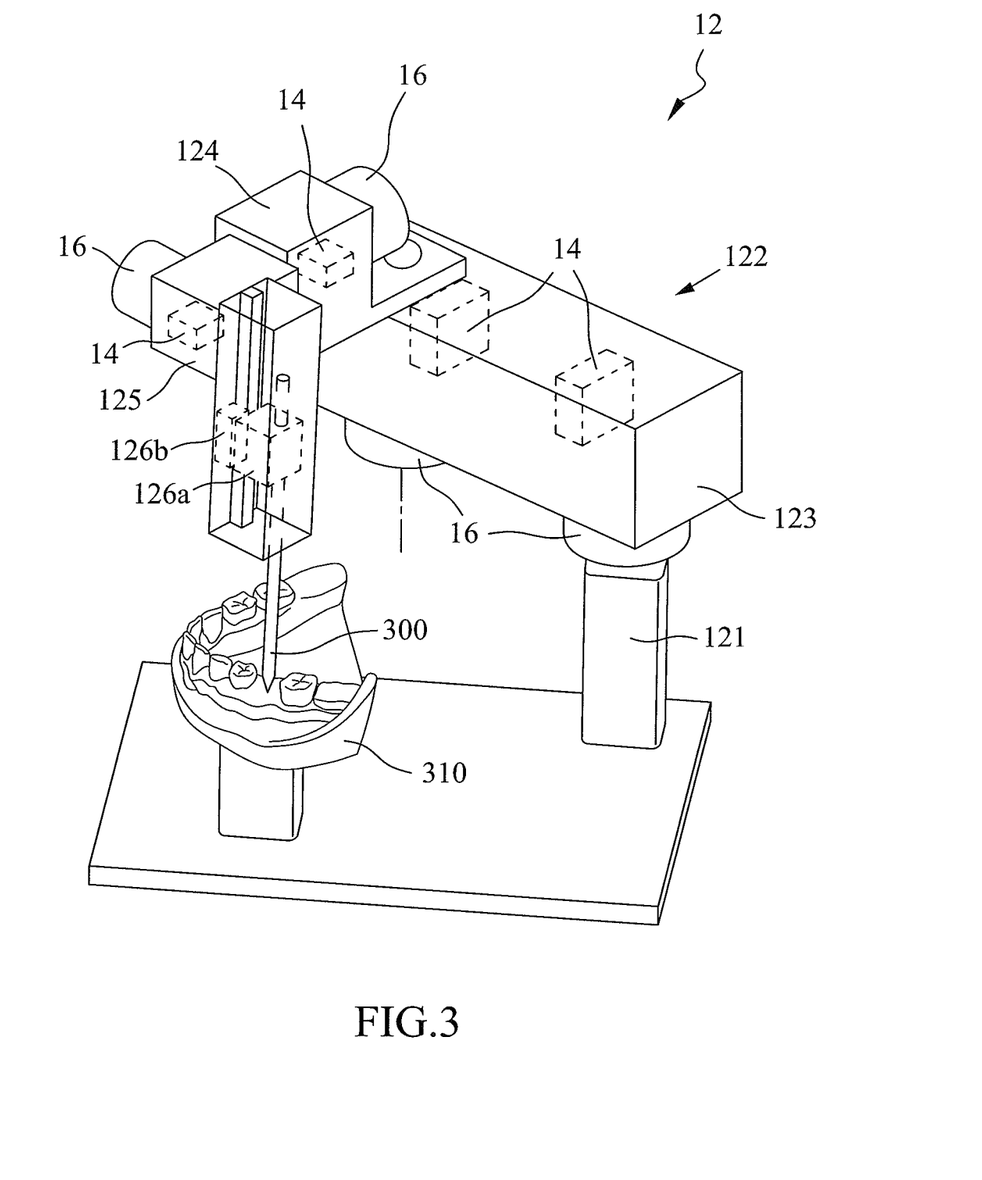
FIG. 3 illustrates an inner structure view of the cast model navigation device of the surgical guide manufacturing system in the present invention.

Furthermore, please refer to FIG. 3 for an inner structure view of the cast model navigation device 10 of the surgical guide manufacturing system 1 in the present invention. As shown in FIG. 3, the positioning module 126 comprises a guiding block 126a for holding the tool 300. The guiding block 126a can move along the axis direction of the tool 300 to adjust the height of the tool 300 and to control the depth of the implant position. In this embodiment, the positioning module 126 can have other forms, such as a ball bearing or other combination structures, and is not limited to the above description.

As shown in FIG. 1 and FIG. 3, the plurality of decoders 14 and the plurality of braking elements 16 are each disposed at points where the first moving element 123 is axially connected with the base 121. The first moving element 123 is axially connected with the second moving element 124, the second moving element 124 is axially connected with the third moving element 125, and the third moving element 125 is axially connected with the positioning module 126. The plurality of decoders 14 can be electrically connected with the controlling module 30 for measuring the movement information of the articulated arm 12 and transmitting the movement information to the computer system 20 via the controlling module 30 for positioning. Additionally, the positioning module 126 further comprises a linear decoder 126b. The linear decoder 126b is electrically connected with the guiding block 126a and the controlling module 30 for measuring the movement information of the guiding block 126a and transmitting the movement information to the computer system 20 via the controlling module 30 for positioning. The plurality of decoders 14 works with the linear decoder 126b to carry the moving status of the articulated arm 12 to obtain the positioning data of the articulated arm 12. In this embodiment, each braking element 16 is an axis braking element. When the articulated arm 12 determines the implant position, the controlling module 30 activates the plurality of braking elements 16 to lock respective rotating axis, thereby locking the implant position for subsequent manufacturing of the surgical guide.

Figure 4:
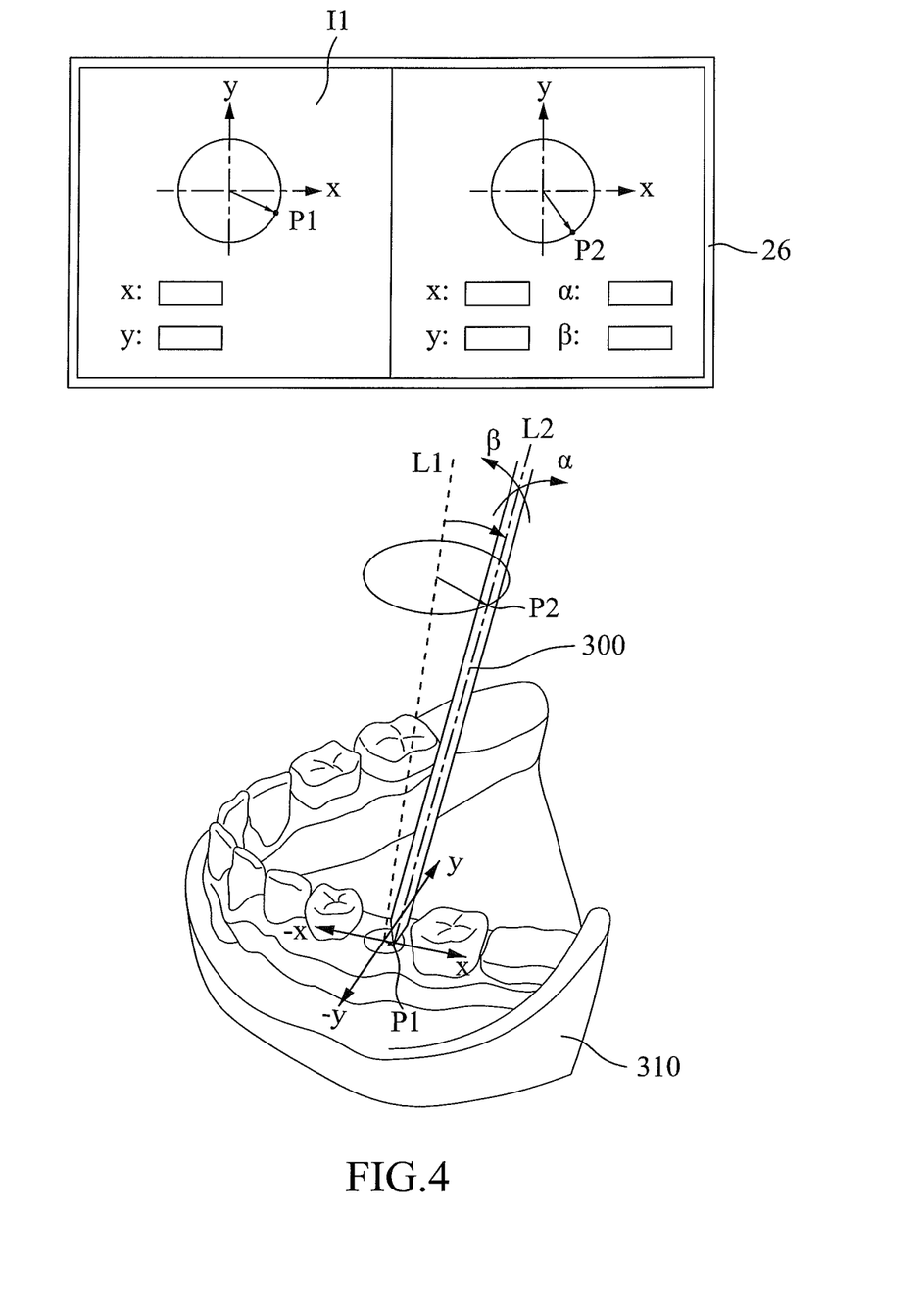
FIG. 4 illustrates an embodiment view of an aided guiding image of the surgical guide manufacturing system in the present invention.

Please refer to FIG. 4 for a view of one embodiment of an aided guiding image of the surgical guide manufacturing system 1 in the present invention. As shown in FIG. 1, in one embodiment of the present invention, when the articulated arm 12 is operated, the computer system 20 can show an aided guiding image corresponding to the operation of the tool 300 via the software program 222, to help the user to determine the implant position. The computer system 20 further comprises a display 26 electrically connected with the processor 24 for displaying the aided guiding image in real time. As shown in FIG. 1 and FIG. 4, in this embodiment, the aided guiding image is a reference position guiding image I1. The computer system 20 can receive the implant position information planned or loaded by the user via the software program 222. Suppose that the implant position information corresponds to a target implant position L1. When the tool 300 is operated to move on the cast model 310, the software program 222 can show a pointing position L2 of the tool 300 to be compared with the target implant position L1. As shown in FIG. 4, when the user uses the tool 300 to determine the pointing position L2, the software program 222 is executed to obtain the positioning point P1 of the tool 300 and a predetermined positioning point P2, calculate the offset distance (x,y) and the inclination angle ($\alpha,\beta$) between the positioning points P1 and P2 of the pointing position L2 and the target implant position L1, and show the result in the reference position guiding image I1 for real time comparison for the user to determine an optimal implant position. When the articulated arm 12 is moved to an implant position, the user can manually operate the controlling module 30 to activate the plurality of braking elements 16 to lock the articulated arm 12.

Figure 5:
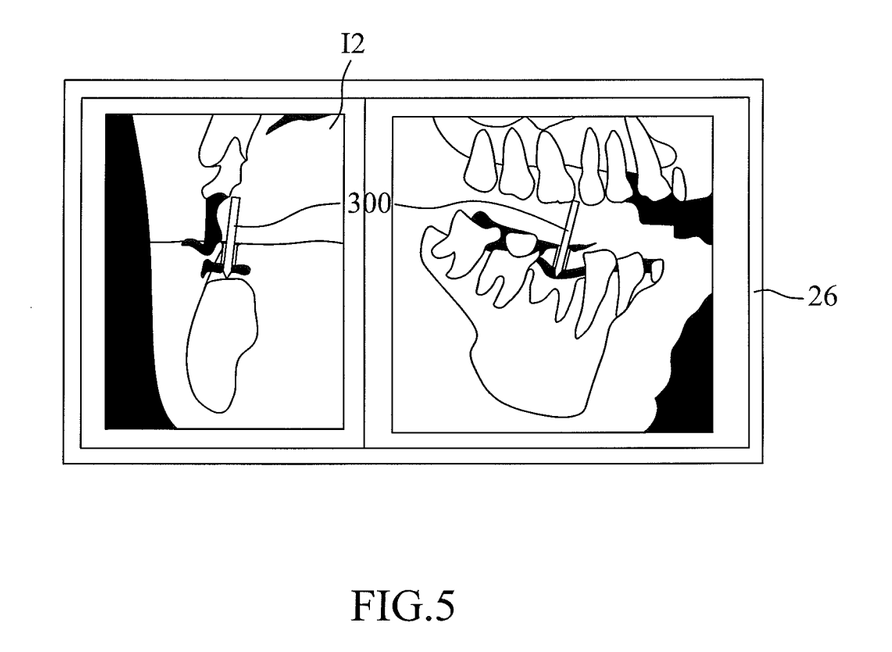
FIG. 5 illustrates another embodiment view of an aided guiding image of the surgical guide manufacturing system in the present invention.

Please refer to FIG. 5 for a view of another embodiment of an aided guiding image of the surgical guide manufacturing system 1 in the present invention. As shown in FIG. 1 and FIG. 5, in this embodiment, the aided guiding image is an anatomical guiding image I2. The anatomical guiding image I2 is obtained from the plurality of CT images 224 to show the cross-sectional CT image corresponding to the part of the patient's jaw under the tool 300 for the user to determine the implant position. While the articulated arm 12 is moving to the implant position, it is possible to use the manual method described above to lock the articulated arm 12. By using the anatomical guiding image I2, it is able to clearly identify the bone structure and tissues of the patient's oral cavity for the user to make a plan immediately to determine the optimal implant position. Then, it is possible to manufacture an accurate surgical guide to avoid error caused by unascertained bone shape in dental implant surgery.

Figure 6:
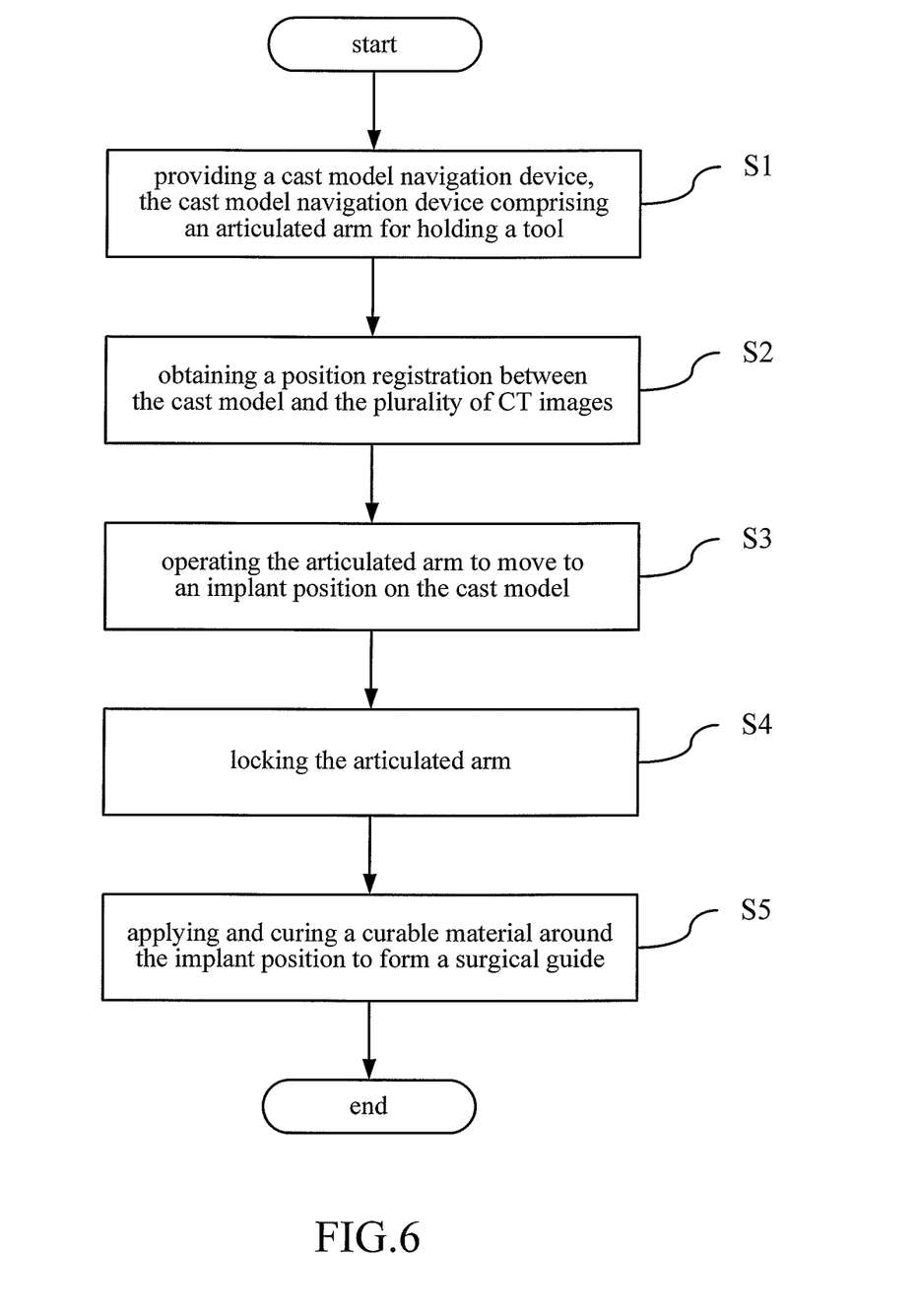
FIG. 6 illustrates a flowchart for a surgical guide manufacturing method in the present invention.

Please refer to FIG. 6 for a flowchart illustrating a surgical guide manufacturing method in the present invention. It is noted that although the following description uses surgical guide manufacturing system 1 in FIG. 1 to illustrate the surgical guide manufacturing method, the present invention is not limited to using the surgical guide manufacturing system 1. Other systems having structures similar to that of the surgical guide manufacturing system 1 are also applicable. As shown in FIG. 6, the surgical guide manufacturing method comprises step S1 to step S5, which will be described in detail.

Step S1: Providing a cast model navigation device 10, with the cast model navigation device 10 including an articulated arm 12 for holding a tool 300. As shown in FIG. 1 and FIG. 2, the cast model navigation device 10 comprises an articulated arm 12, a plurality of decoders 14, and a plurality of braking elements 16. In this embodiment, the articulated arm 12 comprises a base 121 and a moving element set 122. The moving element set 122 comprises a first moving element 123, a second moving element 124, a third moving element 125, and a positioning module 126. The above elements of the moving element set 122 are axially connected with each other to form the articulated arm 12, which can move with four degrees of freedom. However, the articulated arm 12 can have other degrees of freedom. The plurality of decoders 14 and the plurality of braking elements 16 are each disposed respectively at connecting points between the elements of the moving element set 122. The plurality of decoders 14 measures the movement information of the articulated arm 12, and the plurality of braking elements 16 is provided for locking the articulated arm 12. The positioning module 126 comprises a guiding block 126a for holding the tool 300. The guiding block 126a can move linearly along the axis of the tool 300 to adjust the height of the tool 300.

Step S2: Obtaining a position registration between the cast model 310 and the plurality of CT images 224. As shown in FIG. 1 and FIG. 3, the plurality of decoders 14 and the linear decoder 126b of the cast model navigation device 10 can measure the movement information of the articulated arm 12 and the guiding block 126a. The controlling module 30 is provided for transmitting the movement information to the computer system 20. The controlling module 30 accesses the movement information and controls the activation or deactivation of the plurality of braking elements 16. The computer system 20 comprises the memory 22 and the processor 24. The memory 22 stores the software program 222 and the plurality of CT images 224. The processor 24 is electrically connected with the memory 22 to execute the software program 222.

Figure 7A:
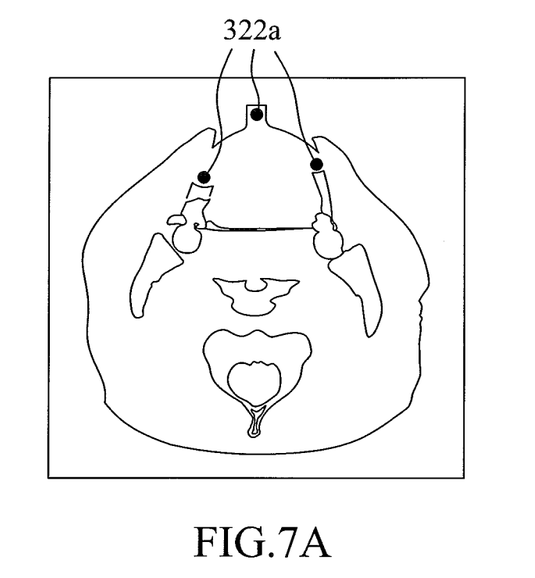
FIG. 7A illustrates an operational view of using the surgical guide manufacturing method in the present invention to obtain the position of the markers from the plurality of CT images.
Figure 7B:
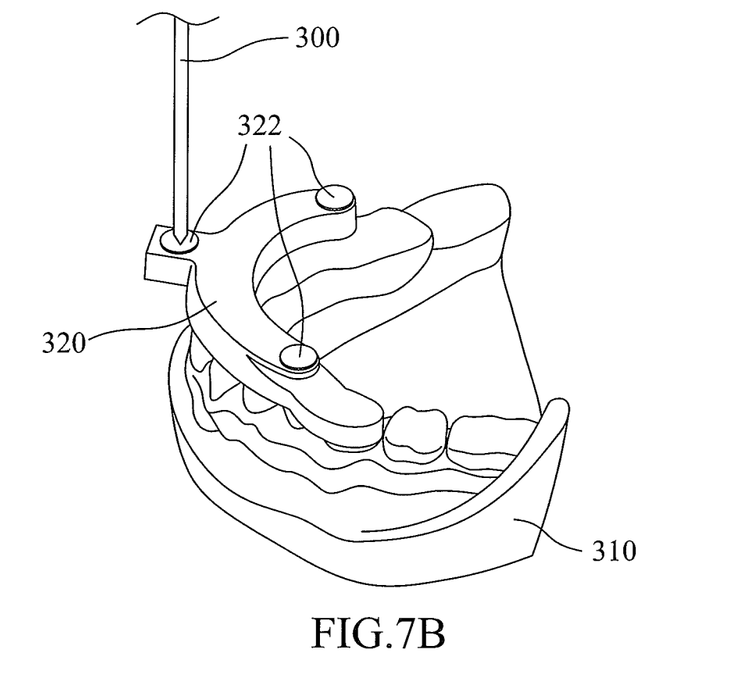
FIG. 7B illustrates an operational view of using the surgical guide manufacturing method in the present invention to obtain the position of the markers on the cast model.

Please refer to FIGS. 7A and 7B for operational views of using the surgical guide manufacturing method in the present invention to obtain the position registration between the cast model 310 and the plurality of CT images 224. The dentist can have the patient wear the CT scan appliance 320 made before the surgery to obtain a plurality of CT images 224 having the plurality of marker images 322a, as shown in FIG. 7A. Then, as shown in FIG. 7B, the CT scan appliance 320 is mounted on the patient's cast model 310. The tool 300 of the cast model navigation device 10 detects the position of the markers 322, and the software program 222 uses the position data to obtain the position registration between the positioning information of the plurality of markers 322 measured by the tool 300 and the plurality of marker images 322a of the plurality of CT images 224 to facilitate the subsequent image processing in real time for navigation. Using the cast model 310 to simulate the dental implant surgery can reduce the number of office visits for the patient. It also provides the dentist a most favorable cast model environment for planning and simulating the surgery.

Step S3: Operating the articulated arm 12 to move to an implant position on the cast model 310. As shown in FIG. 1, the user can move the articulated arm 12 on the cast model 310 to determine an optimal implant position for surgery. When the software program 222 obtains a position registration between the cast model 310 and the plurality of CT images 224, it is possible to obtain the movement information of the articulated arm 12 by moving the articulated arm 12 on the cast model 310. Therefore, when the implant position is selected by the user via the articulated arm 12, the movement information of the articulated arm 12 corresponding to the implant position is obtained. The controlling module 30 can store the movement information. When the articulated arm 12 is once again moved to the implant position in accordance with the movement information, the controlling module 30 can send out a signal to activate the plurality of braking elements 16.

Furthermore, in step S3, the computer system 20 can receive an implant position information corresponding to the implant position planned or loaded by a user via the software program in advance, and the software program converts the implant position information into the movement information corresponding to the implant position of the articulated arm 12. The computer system 20 transmits the movement information to the controlling module 30 to serve as a reference for the articulated arm 12. When the articulated arm 12 is moved to a position corresponding to the movement information, the controlling module 30 can send out a signal to activate the plurality of braking elements 16.

Furthermore, in step S3, after the software program 222 obtains a position registration between the cast model 310 and the plurality of CT images 224, the processor 24 can execute the software program 222 for image processing. When the tool 300 is operated to change the pointing position on the cast model 310, the aided guiding image is updated corresponding to the pointing position of the tool 300 to show an image of a different position. In addition, the user can use the aided guiding image with the implant position information of the computer system 20 to determine the optimal implant position. Also shown in FIG. 4 and FIG. 5, in this embodiment of the present invention, the aided guiding image can be the reference position guiding image I1 or the anatomical guiding image I2, depending on the dental implant surgery plan or the user's preferences. However, the aided guiding image can be other types of images.

Step S4: Locking the articulated arm 12. As shown in FIG. 3, the plurality of braking elements 16 is disposed at the points where the elements of the articulated arm 12 are axially connected with each other. When the articulated arm 12 is moved to the implant position in step S3, the controlling module 30 automatically activates the plurality of braking elements 16, or the user manually operates the controlling module 30 to activate the plurality of braking elements 16 to lock each rotating axis to fix the articulated arm 12. Therefore, the tool 300 held by the articulated arm 12 can remain at the designated implant position for manufacturing of the surgical guide.

Figure 8A:
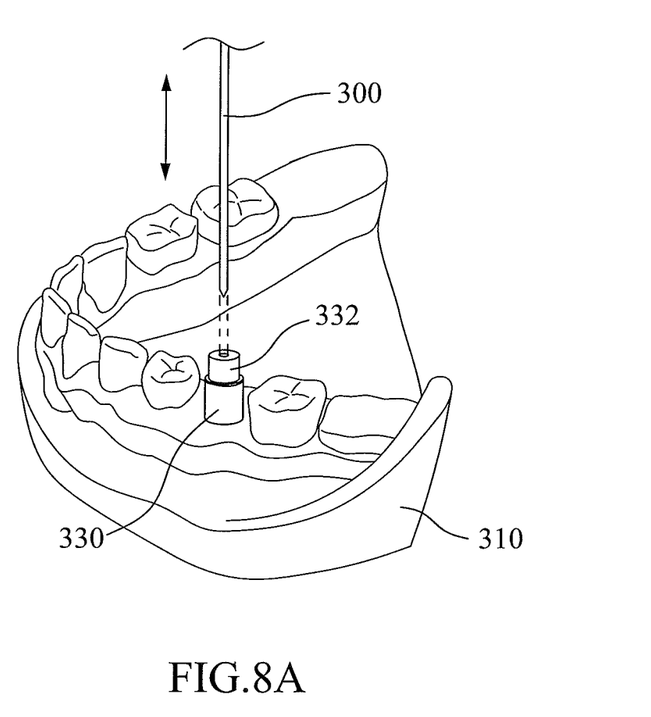
FIG. 8A presents an illustration of the surgical guide manufacturing method in the present invention to decide an implant position on the cast model by a tool.

Finally, step S5: Applying and curing a curable material 340 around the implant position to form a surgical guide 350. When the articulated arm 12 is locked and fixed at the implant position, the user can use the curable material 340 to form the surgical guide 350 based on the implant position. Please refer to FIGS. 8A, 8B and 8C for views of using the surgical guide manufacturing method in the present invention to manufacture the surgical guide 350. As shown in FIG. 1 and FIG. 8A, when the articulated arm 12 is locked, the tool 300 remains at the implant position and points to the surgery target on the cast model 310 to simulate the actual operation of the tool 300 in the dental implant surgery. The user can place a metal ring 330 on the cast model 310, with the position of the metal ring 330 corresponding to the implant position. According to the size of the tool 300, it is possible to insert the tool 300 having a cross-sectional diameter corresponding to the inner diameter of the metal ring 330 into the metal ring 330, or as the present invention illustrates, a sleeve element 332 is inserted in the metal ring 330, and the aperture of the sleeve element 332 corresponds to the cross-sectional diameter of the tool 300.

Figure 8B:
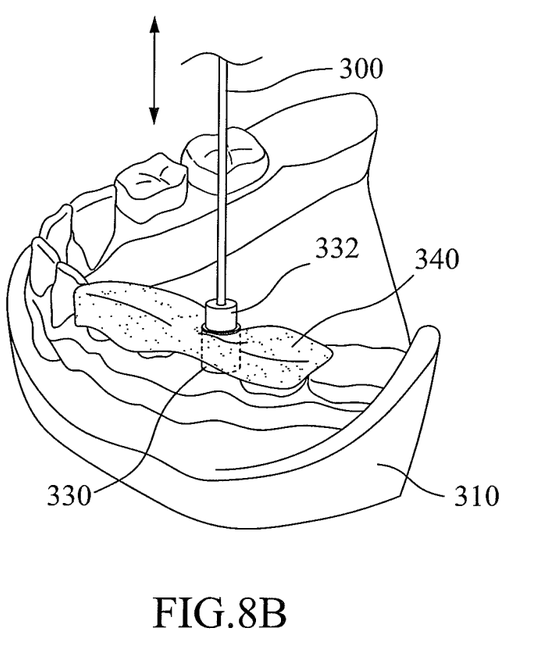
FIG. 8B presents an illustration of the surgical guide manufacturing method in the present invention to move down the tool along the implant position to manufacture the surgical guide.

As shown in FIG. 8B, the tool 300 is moved down along the implant position to be inserted into the sleeve element 332. The metal ring 330 and the sleeve element 332 are then fixed. Thereafter, the curable material 340 is spread around the metal ring 330 and its neighboring cast model 310 to cover the metal ring 330. When the curable material 340 is cured, the tool 300 is pulled out, the sleeve element 332 is removed, and the shaped curable material 340 is removed from the cast model 310 to form a surgical guide 350 with a corresponding hole 352 corresponding to the target implant position. In this embodiment, the curable material 340 can be a light-cured resin material which is cured under exposure to light of a certain wavelength. However, the curable material 340 can be other kinds of curable material.

Figure 8C:
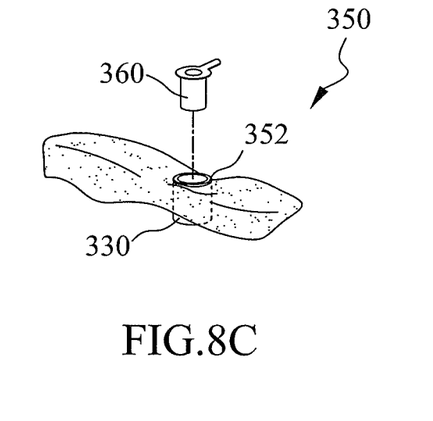
FIG. 8C presents an illustration of the surgical guide manufacturing method in the present invention to form the surgical guide.

Also as shown in FIG. 8C, the corresponding hole 352 of the surgical guide 350 is protected and positioned by the metal ring 330. In addition, the corresponding hole 352 can accept various kinds of metal guiding sleeves 360 to accommodate surgery tools of different sizes and forms. When the dentist is performing the surgery, he/she can place the surgical guide 350 in the surgery area securely across the remaining teeth. Then, the surgery tool can be precisely and steadily guided by the metal ring 330 down to the planned location along the optimal implant position. The dentist can change the surgery tool if necessary in accordance with different clinical situations.

Figure 9A:
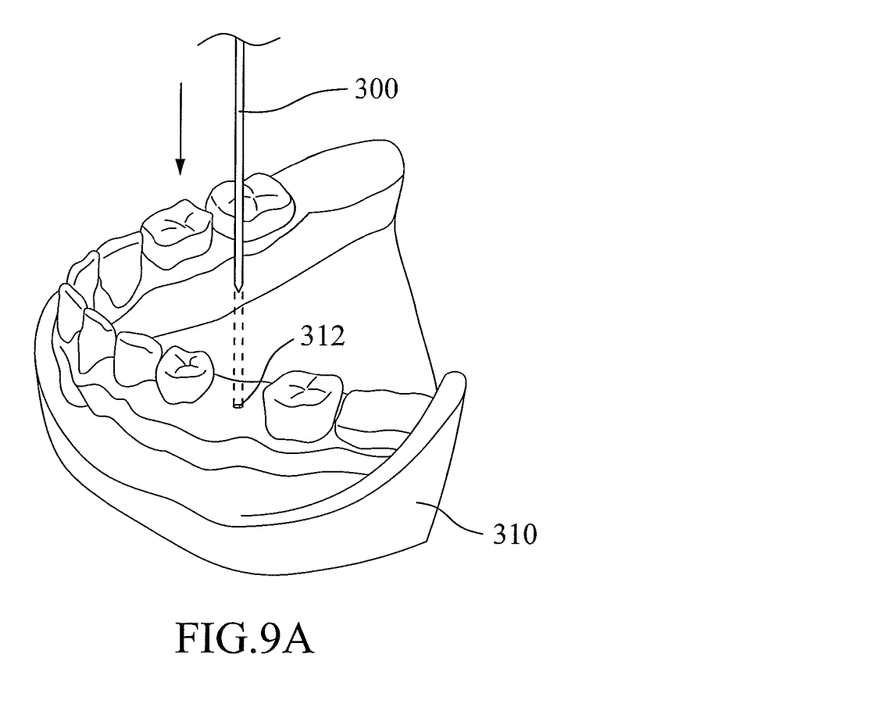
FIG. 9A presents an illustration of the surgical guide manufacturing method in the present invention to decide an implant position on the cast model by a tool in another embodiment.
Figure 9B:
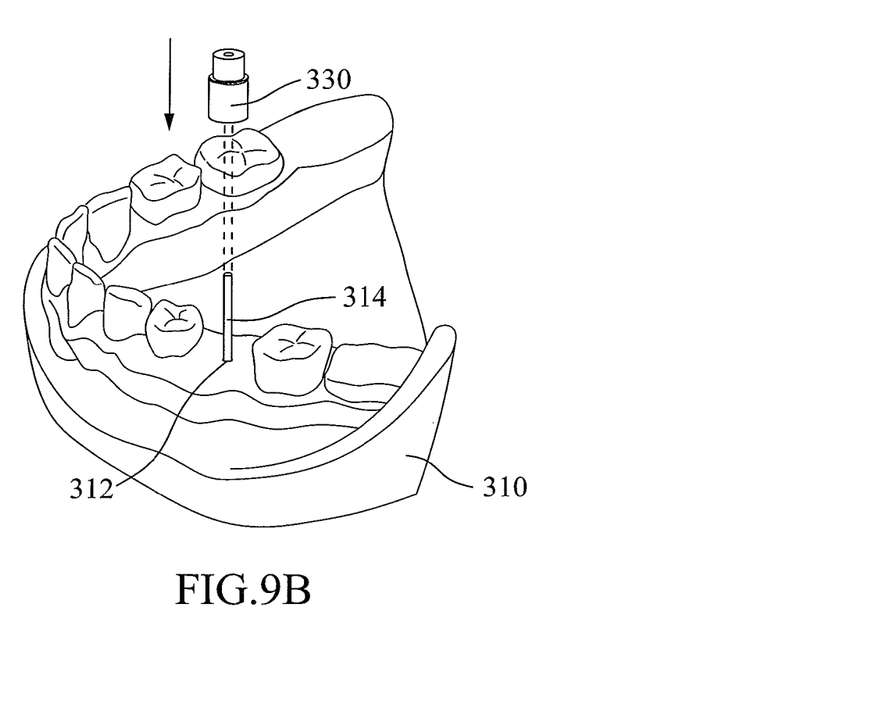
FIG. 9B presents an illustration of the surgical guide manufacturing method in the present invention to place the metal ring on the cast model through a positioning pole in another embodiment.

Please refer to FIGS. 9A and 9B for views of using the surgical guide manufacturing method in the present invention to manufacture the surgical guide 350 in another embodiment. As shown in FIGS. 9A and 9B, in another embodiment of the present invention, the user uses the tool 300 to drill a mounting hole 312 on the cast model along the implant position. The user can inset a positioning pole 314 in the mounting hole 312 after the tool 300 is moved away, insert the metal ring 330 or the combination of the metal ring 330 and the sleeve element 332 through the positioning pole 314, and then apply the curable material around the metal ring 330 and the neighboring cast model 310. When the curable material 340 is cured, the positioning pole 314 is pulled out and removed from the cast model 310, thereby forming the surgical guide 350.

In other embodiments of the present invention, it is possible to manufacture an unfinished surgical guide 350 with a through hole, which is substantially located at the implant surgery area. When the user determines the implant position, he/she places the metal ring 330 in the through hole corresponding to the implant position. Then, he/she inserts the tool 300 into the metal ring 330 and applies a suitable amount of the curable material 340 to fill the gap between the through hole and the metal ring 330. The tool 300 is pulled out after the curable material 340 is cured, thereby forming the surgical guide 350. However, it is noted that the curing method is not limited to the above embodiments.

It is noted that the above-mentioned embodiments are only for illustration. It is intended that the present invention cover modifications and variations of this invention provided they fall within the scope of the following claims and their equivalents. Therefore, it will be apparent to those skilled in the art that various modifications and variations can be made to the structure of the present invention without departing from the scope or spirit of the invention.

What is claimed is:

1. A surgical guide manufacturing method for dental implant surgery planning comprising obtaining a cast model of a patient's jaw, making a CT scan appliance with a plurality of radiopaque markers out of the cast model, and having the patient wear the CT scan appliance to obtain a plurality of CT images of the patient's jaw and teeth, the method comprising:

providing a cast model navigation device, with the cast model navigation device comprising an articulated arm for holding a tool, a plurality of decoders and a plurality of braking elements each disposed at connecting points of a plurality of elements of the articulated arm, respectively;

measuring movement information of the articulated arm using the plurality of decoders;

electrically connecting the cast model navigation device with a computer system via a controlling module, with the controlling module obtaining the movement information and controlling the activation or deactivation of the plurality of braking elements; wherein the computer system comprises a software program;

obtaining a position registration between the cast model and the plurality of CT images, wherein the position registration between the cast model and the plurality of CT images is obtained by operating the articulated arm to measure positions of the markers of the CT scan appliance mounted on the cast model by using the software program;

operating the articulated arm to move to an implant position on the cast model, wherein the software program is executed to show an aided guiding image corresponding to operation of the articulated arm to move on the cast model in real time for the user to determine the implant position, and wherein the aided guiding image is an anatomical guiding image showing the CT image corresponding to a part of the patient's jaw under the tool for the user to determine the implant position;

locking the articulated arm at the implant position using the plurality of braking elements; and when the articulated arm is locked at the implant position applying and curing a curable material around the implant position to form a surgical guide.

2. The surgical guide manufacturing method as claimed in claim 1, wherein in operating the articulated arm to move to the implant position on the cast model, the controlling module stores the movement information corresponding to the implant position;

and wherein, when the articulated arm is once again moved to the implant position in accordance with the movement information, the controlling module activates the plurality of braking elements to lock the articulated arm.

3. The surgical guide manufacturing method as claimed in claim 1, wherein in operating the articulated arm to move to the implant position on the cast model, the computer system receives an implant position information corresponding to the implant position planned or loaded by the user via the software program, and wherein the software program converts the implant position information into the movement information corresponding to the implant position; and wherein, when the articulated arm is operated to move to the implant position in accordance with the movement information, the controlling module activates the plurality of braking elements to lock the articulated arm.

4. The surgical guide manufacturing method as claimed in claim 1, wherein the curable material covers a metal ring corresponding to the implant position.

* * * * *